United States Patent [19]

Izumori et al.

[11] Patent Number: 5,679,562
[45] Date of Patent: Oct. 21, 1997

[54] D-KETOHEXOSE 3-EPIMERASE, AND ITS PREPARATION

[75] Inventors: Ken Izumori, Kagawa; Keiji Tsusaki, Okayama, both of Japan

[73] Assignee: Kabushiki Kaisha Hayashibara Seibutsu Kagaku Kenkyujo, Okayama, Japan

[21] Appl. No.: 413,937

[22] Filed: Mar. 30, 1995

Related U.S. Application Data

[63] Continuation of Ser. No. 132,853, Oct. 7, 1993, Pat. No. 5,411,880.

[30] Foreign Application Priority Data

Oct. 8, 1992 [JP] Japan ................................. 4-312580

[51] Int. Cl.$^6$ ......................................................... C12N 9/90
[52] U.S. Cl. ........................... 435/233; 435/94; 435/183; 435/280
[58] Field of Search ............................... 435/183, 233, 435/94, 280

[56] References Cited

U.S. PATENT DOCUMENTS

| | | | |
|---|---|---|---|
| 4,800,161 | 1/1989 | Ebeling et al. | |
| 4,988,822 | 1/1991 | Asada et al. | 435/121 |
| 5,085,993 | 2/1992 | Fujiwara | 435/138 |
| 5,168,056 | 12/1992 | Frost | 435/183 |
| 5,411,880 | 5/1995 | Izumori et al. | 435/233 |

FOREIGN PATENT DOCUMENTS

| | | |
|---|---|---|
| 0173919 | 3/1986 | European Pat. Off. . |
| 0304021 | 2/1989 | European Pat. Off. . |
| 3266996 | 11/1991 | Japan . |

OTHER PUBLICATIONS

Enzyme Nomenclature, (San Diego, CA: Academic Press Inc., 1992), pp. 496–498.

Chemical Abstracts, vol. 116 (1992), 116: 12703d, pp. 718–719.

A. R. Khan et al, "D–Sorbose Fermentation" from Galactitol by Pseudomonas sp. ST 24, Journal Of Fermentation and Bioengineering, vol. 74, No. 3, 1992.

K. Izumori et al, A New Enzyme, D–Ketohexose 3–Epimerase, from Pseudomonas sp. ST–24, Bioscience, Biotechnology, And Biochemistry, vol. 57, Jun. 1993.

Primary Examiner—Herbert J. Lilling
Attorney, Agent, or Firm—Browdy and Neimark

[57] ABSTRACT

D-ketohexose 3-epimerase, a novel epimerase, is obtained by cultivating bacteria of the genus Pseudomonas including *Pseudomonas cichorii* ST-24 (FERM BP-2736). D-Ketohexose 3-epimerase epimerizes D-ketohexose, D-ketopentose and L-ketopentose at their C-3 positions to form their corresponding epimeric counterparts in a high yield at a high conversion rate. Interconversion reaction using D-Ketohexose 3-epimerase yields mixture of intact ketose and its epimeric counterpart which can impart an appropriate sweetness, gloss and improve taste quality when used in foods, beverages, feeds, pet foods, dentifrice, cachou, sublingual agents and internal medicines.

3 Claims, 8 Drawing Sheets

D-KETOHEXOSE 3-EPIMERASE, AND ITS PREPARATION

CROSS-REFERENCE TO RELATED APPLICATIONS

This is a continuation of application Ser. No. 08/132,853, filed Oct. 7, 1993, now U.S. Pat. No. 5,411,880.

BACKGROUND OF THE INVENTION

1. Field of the Invention

The present invention relates to D-ketohexose 3-epimerase, and its preparation and uses.

2. Description of the Prior Art

As described in Enzyme Nomenclature published by Academic Press Inc., USA, 1992, epimerases act on various saccharides. Since conventional epimerases such as ribulose-phosphate 3-epimerase (EC 5.1.3.1) and UDP glucose 4-epimerase (EC 5.1.3.2), however, mainly act on saccharides coupled with phosphates or UDP, they are not usable in industrial-scale production of free neutral saccharides. There has been known only two epimerases, i.e, aldose 1-epimerase (EC 5.1.3.3) and cellobiose epimerase (EC 5.1.3.11), which act on free saccharides. The former catalyzes the epimerization between α- and β-anomers of aldoses at their C-1 positions, while the latter catalyzes the epimerization between α- and β-anomers of cellobiose. Although there has been a great demand for epimerases which act on free ketoses, the existence of such has not been confirmed.

It has been in a great demand to obtain a ketose epimerase which acts on free ketoses, and also to establish its preparation and uses.

SUMMARY OF THE INVENTION

We have screened various epimerases which readily epimerize free ketopentoses and ketohexoses into their corresponding epimeric ketopentoses and ketohexoses. As a result, we eventually found D-ketohexose 3-epimerase and established its production as well as establishing a method of converting D-ketohexose, D-ketopentose and L-ketopentose using the enzyme, a process of producing converted ketoses, and a process of producing sweetener containing the same. Thus, we completed this invention. More particularly, the D-ketohexose 3-epimerase of the invention is a novel enzyme which has an activity of epimerizing D-ketohexose at its C-3 position into its corresponding epimeric D-ketohexose, and shows the following physicochemical properties:

1. Action and substrate specificity Epimerizing D-ketohexose at its C-3 position into its corresponding epimeric D-ketohexose. Epimerizing D- and L-ketopentoses at their C-3 positions into their corresponding epimeric D- and L-ketopentoses;
2. Optimum pH and pH stability Possessing an optimum pH of 7–10 and being stable at pH 5–10;
3. Optimum temperature and thermal stability Possessing an optimum temperature of around 60° C., and being stable at temperature up to 50° C.; and
4. Ultraviolet absorption spectrum Exhibiting an absorption at a wavelength of 275–280 nm.

BRIEF EXPLANATION OF THE ACCOMPANYING DRAWINGS

FIG. 1 shows the optimum pH of the present enzyme.
FIG. 2 shows the pH stability of the present enzyme.
FIG. 3 shows the optimum temperature of the present enzyme.
FIG. 4 shows the thermal stability of the present enzyme.
FIG. 5 shows the molecular weight of the present enzyme.
FIG. 6 shows a polyacrylamide gel electrophoretic pattern of the present enzyme.
FIG. 7 shows an infrared absorption spectrum of D-sorbose prepared from D-tagatose by the invention.
FIG. 8 shows an infrared absorption spectrum of a standard D-sorbose.

In FIG. 5, the symbol "A" shows bovine serum albumin (BSA); the symbol "B", ovalbumin; the symbol "C", the present enzyme (D-ketohexose 3-epimerase); the symbol "D", chymotrypsinogen A; and the symbol "E", cytochrome C.

In FIG. 6, the symbol "I" shows the starting point of electrophoresis; the symbol "II", the present enzyme (D-ketohexose 3-epimerase); and the symbol "III", bromophenol blue.

DETAILED DESCRIPTION OF THE INVENTION

Figure 1:
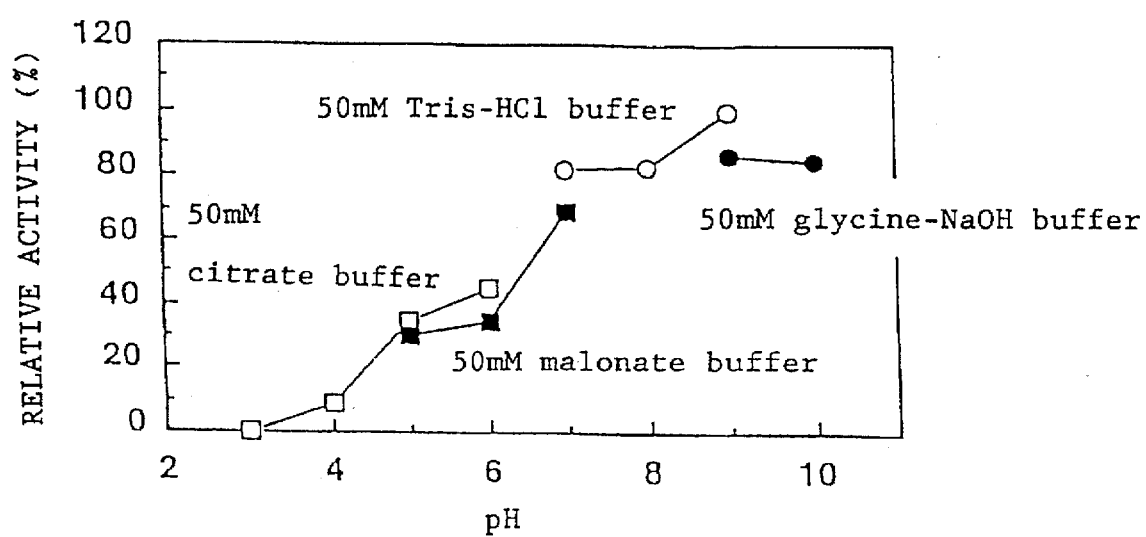

The present invention relates to D-ketohexose 3-epimerase, and its preparation and uses.

We have screened various epimerases which readily epimerize free ketopentoses and ketohexoses into their corresponding epimeric ketopentoses and ketohexoses. As a result, we eventually found D-ketohexose 3-epimerase and established its production as well as establishing a method of converting D-ketohexose, D-ketopentose and L-ketopentose using the enzyme, a process of producing converted ketoses, and a process of producing sweetener containing the same. Thus, we completed this invention. More particularly, the D-ketohexose 3-epimerase of the invention is a novel enzyme which has an activity of epimerizing D-ketohexose at its C-3 position into its corresponding epimeric D-ketohexose, and shows the following physicochemical properties:

1. Action and substrate specificity Epimerizing D-ketohexose at its C-3 position into its corresponding epimeric D-ketohexose. Epimerizing D- and L-ketopentoses at their C-3 positions into their corresponding epimeric D- and L-ketopentoses;
2. Optimum pH and pH stability Possessing an optimum pH of 7–10 and being stable at pH 5–10;
3. Optimum temperature and thermal stability Possessing an optimum temperature of around 60° C., and being stable at temperature up to 50° C.; and
4. Ultraviolet absorption spectrum Exhibiting an absorption at a wavelength of 275–280 nm.

The D-ketohexose 3-epimerase according to the present invention is usually obtained by the cultivation of microorganisms capable of producing D-ketohexose 3-epimerase.

Examples of microorganisms advantageously usable in the invention are bacteria of the genus Pseudomonas including Pseudomonas cichorii ST-24 (FERM BP-2736) and its mutants disclosed in Japanease Patent Laid-Open No. 266, 996/91.

D-ketohexose 3-epimerase is prepared by cultivating such a bacterium in a nutrient culture medium containing carbon sources, nitrogen sources, minerals, vitamins and the like for about 1–5 days, preferably, under aerobic conditions such as aeration-agitation conditions; and recovered from obtained cells and/or supernatant. The resultant culture is usable as a crude D-ketohexose 3-epimerase. If necessary, the culture can be partially purified by conventional methods such as filtration, centrifugation, salting out, dialysis, concentration and lyophilization, prior to its use. In case of a higher purification is required, the culture is purified to the possible highest level by absorption and desorption using an ion-exchanger, gel filtration, isoelectric focussing, electrophoresis, high-performance liquid chromatography (hereinafter abbreviated as "HPLC"), affinity chromatography, and/or absorption and desorption using monoclonal antibodies.

In the conversion reaction wherein one or more members selected from the group consisting of D-ketohexose, D-ketopentose and L-ketopentose are epimerized at their C-3 positions into their corresponding epimeric D-ketohexose, D-ketopentose and L-ketopentose; D-ketohexose 3-epimerase can immobilized in usual manner and advantageously used in repeated or continuous reaction.

The present conversion reaction is usually carried out under the following conditions: Substrate concentration is set in the range of 1–60 w/v %, preferably, about 5–50 w/v %; reaction temperature, in the range of 10°14 70° C., preferably, about 30°14 60° C.; reaction pH, in the range of 5–10, preferably, in the range of about 7–10; and the amount of enzyme, at least one unit per gram of substrate, preferably, 50–5,000 units per gram of substrate. The reaction time can be arbitrarily chosen, usually, in the range of 5–50 hours in a batch reaction from an economical view-point.

Reaction mixtures obtainable by the present conversion reaction, which contain newly formed ketoses and intact ketoses as a starting material, can be advantageously used intact as a sweetener, moisture-imparting agent, crystallization-preventing agent and gloss-imparting agent. The reaction mixtures are usually prepared in usual manner into syrupy products by successive decoloration with activated carbons, salting out with ion-exchange in H- and OH-form, and concentration.

If necessary, the concentrates thus obtained can be easily or readily separated and purified on a column chromatography using strongly-acidic cation exchange of alkaline metal- or alkaline earth metal-form to obtain the newly formed ketoses and the intact ketoses as a starting material, followed by concentrating the ketose-rich fractions into syrupy products. If ketoses are crystallizable, they are advantageously crystallized into crystalline products. Separated ketoses can be advantageously used as a starting material for the next conversion reaction.

The separated ketoses are advantageously usable as a sweetener, in particular, to impart an appropriate sweetness to orally administrable products such as foods, beverages, feeds, pet foods, dentifrice, cachou, sublingual agents and internal medicines, as well as to improve their taste qualities. The ketoses can be also advantageously used as a carbon source for fermentation, as well as chemical reagent, material and intermediate for chemicals and pharmaceuticals.

The following examples will explain the present invention.

EXAMPLE 1

A nutrient culture medium consisting of 0.2 w/v % ammonium sulfate, 0.24 w/v % potassium phosphate monobasic, 0.56 w/v % potassium phosphate dibasic, 0.01 w/v % magnesium sulfate heptahydrate, 0.5 w/v % yeast extract, 1 w/v % D-glucose and deionized water was placed in a jar fermenter, sterilized at 120° C. for 20 minutes, and aseptically inoculated with 1 v/v % of a seed culture of Pseudomonas cichorii ST-24 (FERM BP-2736), followed by the cultivation at 30° C. for 40 hours under aeration-agitation conditions. The cells which had been recovered from 80 liters of the resultant culture were crushed by grinding in the presence of activated alumina and then subjected to extract an enzyme in 50 mM Tris-HCl buffer (pH 7.5).

The obtained crude enzyme solution was purified in the presence of manganese chloride by repeated fractional sedimentation using polyethylene glycol 6,000 (hereinafter abbreviated as "PEG"). The precipitates, which had formed in the crude enzyme solution at the PEG concentrations of 5–18 w/v in the presence of 0.1 M manganese chloride, were dissolved in a fresh preparation of the same buffer. The crude enzyme solution was further purified by the above fractional sedimentation. The resultant solution was heated at 50° C. for 20 minutes, and the resultant degenerated proteins were removed by centrifugation. The resultant product was purified by allowing it to absorb on "DEAE-TOYOPEARL® 650M", a product of Tosho Corporation, Tokyo, Japan, and eluting the absorbed substance with potassium chloride solution. The purified product thus obtained was demineralized on an ultrafiltration using "Toyo Roshi UK-10", a filter membrane commercialized by Toyo Roshi Kaisha Ltd., Tokyo, Japan, concentrated and purified on a gel filtration using "Sephadex® G150", a product of Pharmacia, Uppsala, Sweden. Fractions with an activity were concentrated and purified on an isoelectric focussing using "Ampholine®", a product of Pharmacia, Uppsala, Sweden.

The enzyme specimen thus obtained was assayed as follows: The reaction solution used in this assay consisted of 100 microliters 50 mM Tris-HCl buffer (pH 7.5), 50 microliters 40 mM D-tagatose and 50 microliters of an enzyme solution. The enzymatic reaction was carried out at 30° C. for 60 minutes, and the formed D-sorbose was quantitated on HPLC. One unit of the enzyme activity is defined as the amount of enzyme that epimerizes one micromol of D-tagatose per one minute.

The purification procedure was as shown in Table 1.

TABLE 1

| Purification step | Protein (mg) | Enzyme activity (unit) | Yield (%) | Purification degree (fold) |
|---|---|---|---|---|
| Crude extract | 42,100 | 52,000 | 100.0 | 1 |
| PEG (first) | 8,380 | 50,600 | 97.3 | 4.9 |
| PEG (second) | 3,760 | 26,400 | 50.8 | 5.7 |
| Heat treatment | 3,210 | 27,800 | 53.5 | 7.0 |
| DEAE-TOYOPEARL ® | 415 | 17,200 | 33.1 | 33.6 |
| Sephadex ® G150 | 127 | 16,800 | 32.3 | 106 |
| Isoelectric focussing | 3.0 | 1,078 | 2.1 | 290 |

As obvious from the results in Table 1, the purification step improved the specific activity of a crude enzyme by about 290 folds, and gave the yield of about 2%. The physicochemical properties of the present D-ketohexose 3-epimerase were studied with the finally obtained sample of these purification steps:

(1) Action and substrate specificity

D-ketohexose 3-epimerase acts on all of the four D-ketohexoses (D-tagatose, D-sorbose, D-fructose and D-psicose) among eight D- and L-ketohexoses, and epimerizes them at their C-3 positions into their corresponding epimeric D-ketohexoses. It acts on all four D- and L-ketopentoses (D- and L-xyluloses, D- and L-ribuloses), and epimerizes them at their C-3 positions into their corresponding epimeric D- and L-ketopentoses.

The enzyme most strongly catalyzed each interconversion reaction of D-tagatose and D-sorbose. The activity in the interconversion reactions of D-fructose and D-psicose was about 30–40% of that in each interconversion reaction D-tagatose and D-sorbose. While the activity in the interconversion reaction between D- and L-ketohexoses was about 10–30% of that in D-tagatose and D-sorbose. All the reactions were reversible- and equilibrium-reactions and did not require coenzymes and metal ions.

(2) Optimum pH and pH stability

The Optimum pH of the enzyme was determined in accordance with the aforementioned enzyme assay. The results were as shown in FIG.1. In the figure, the symbol "-□-" shows 50 mm citrate buffer; the symbol "-■-", 50 mM malonate buffer; the symbol "-○-", 50 mM Tris-HCl buffer; and the symbol "-●-", 50 mM glycine-NaOH buffer. As is obvious from FIG. 1, the optimum pH was 7–10.

Figure 2:
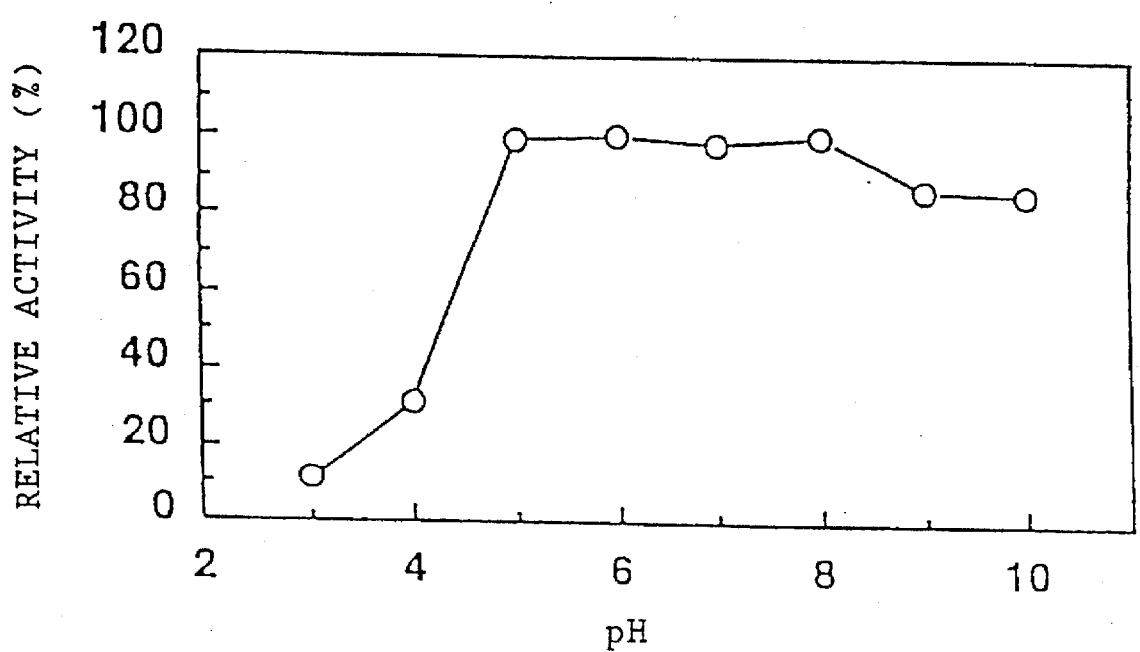

The pH stability of the enzyme was studied by incubating it at 30° C. for 60 minutes, then measuring the residual activity. The results were as shown in FIG. 2. As is obvious from FIG. 2, the enzyme was stable at pH 5–10.

(3) Optimum temperature and thermal stability

Figure 3:
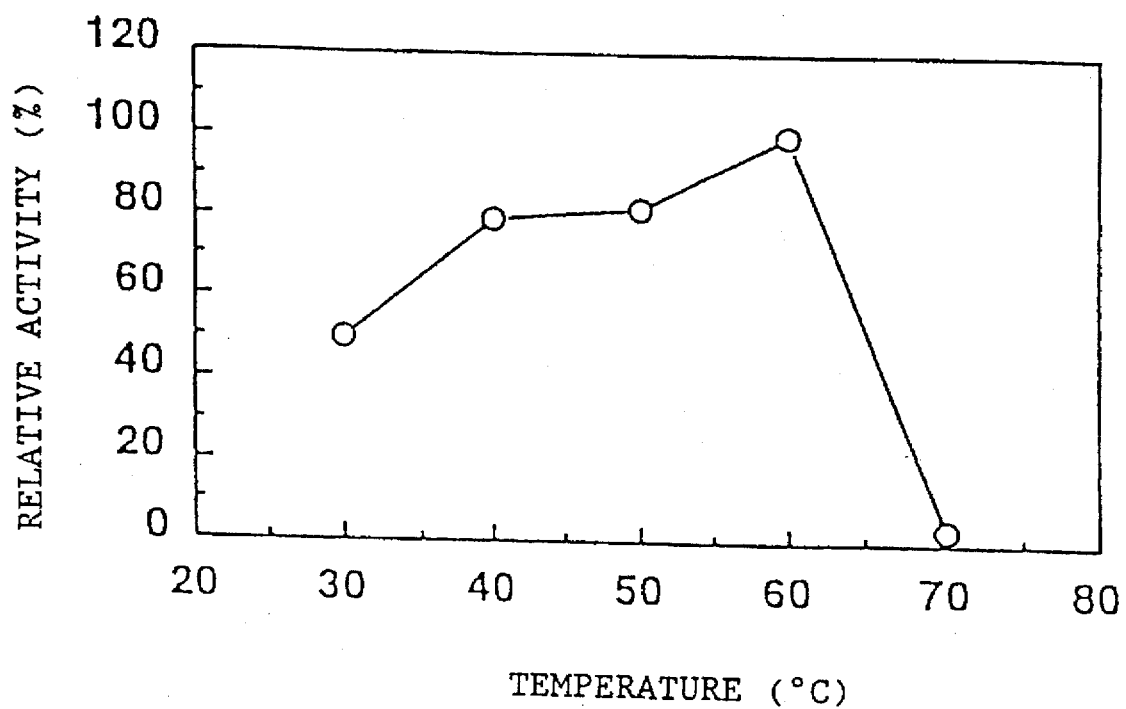
Figure 4:
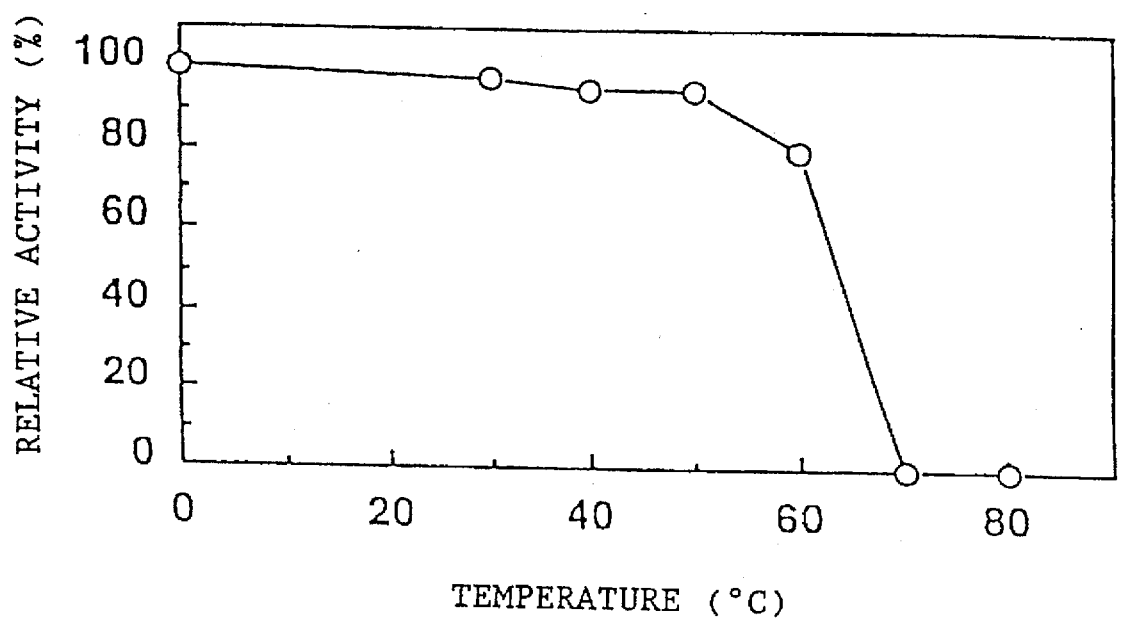

The optimum temperature of the enzyme was determined in accordance with the aforementioned enzyme assay. From the results as shown in FIG. 3, the optimum temperature was around 60° C. The thermal stability was studied by incubating it in 50 mM Tris-HCl buffer (pH 7.5) at different temperatures for 10 minutes, then determining the residual activity. As is obvious from FIG. 4, the enzyme was stable at a temperature up to 50° C.

(4) Ultraviolet absorption spectrum

The enzyme exhibits an absorption at a wavelength of 275–280 nm.

(5) Molecular weight

Figure 5:
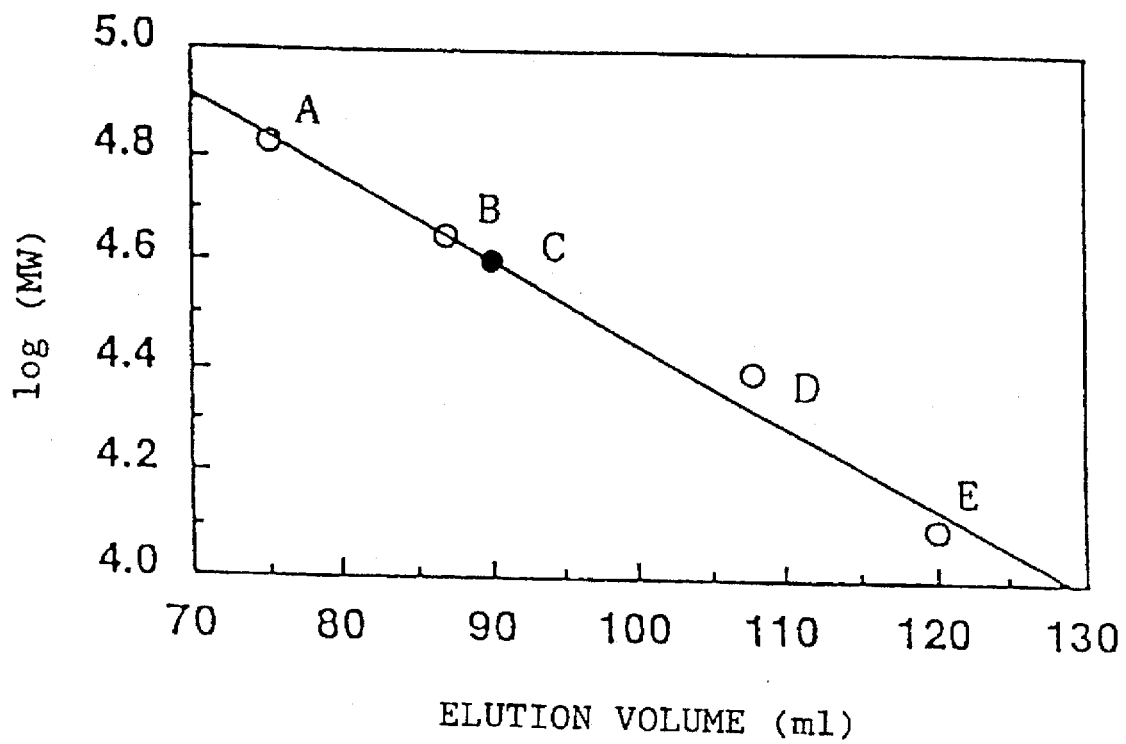

The molecular weight of the enzyme was determined on a gel filtration chromatography using a column (1.2×100 cm) packed with "Sephadex®G150" wherein 25 mM Tris-HCl buffer (pH 7.5) was used as an eluent and subjected to the column at a flow rate of 0.15 ml/min. The results were as shown in FIG. 5. In the figure, the symbol "A" shows bovine serum albumin, 67,000 dalton; the symbol "B", ovalbumin, 45,000 dalton; the symbol "C", the present enzyme; the symbol "D", chymotrypsinogen A, 25,000 dalton; and the symbol "E", cytochrome C, 12,500 dalton. As is obvious from FIG. 5, the molecular weight of the enzyme (C) was determined as 41,000±3,000, based on a standard curve which was made by plotting the molecular weights of proteins A, B, D and E which had been known.

(6) Isoelectric point

Upon analysis on an isoelectric focussing using "Ampholine®", the enzyme showed an isoelectric point of the enzyme is pH 4.3±0.2.

(7) Polyacrylamide gel electrophoresis

Figure 6:
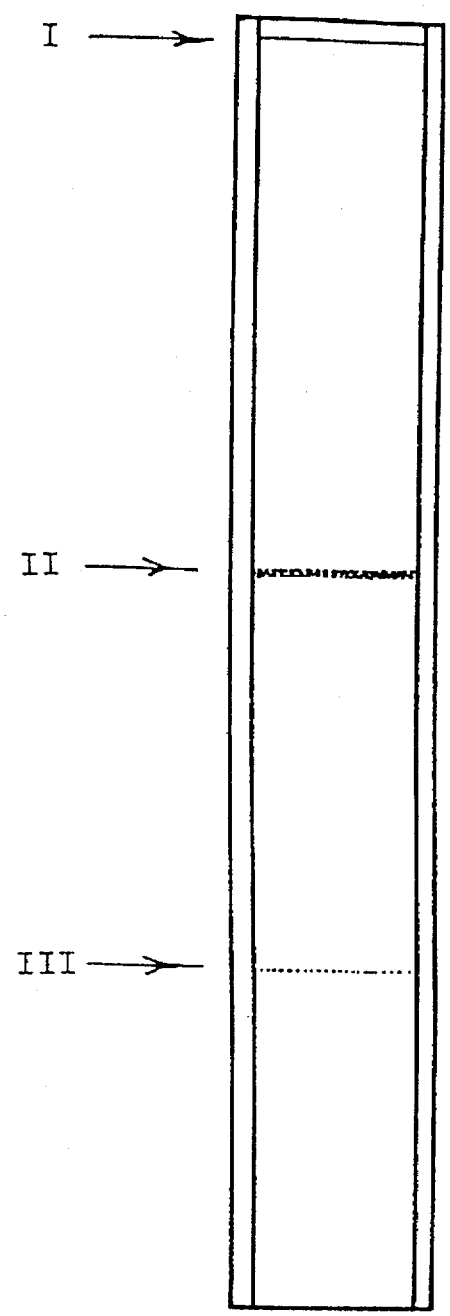

FIG. 6 shows a polyacrylamide gel electrophoretic pattern of the enzyme. In the figure, the symbol "I" shows the starting point; the symbol "II", the present enzyme; and the symbol "III", bromophenol blue. As is obvious from FIG. 6, the enzyme showed a single band.

EXAMPLE 2

Interconversion reaction of D-tagatose and D-sorbose

Figure 7:
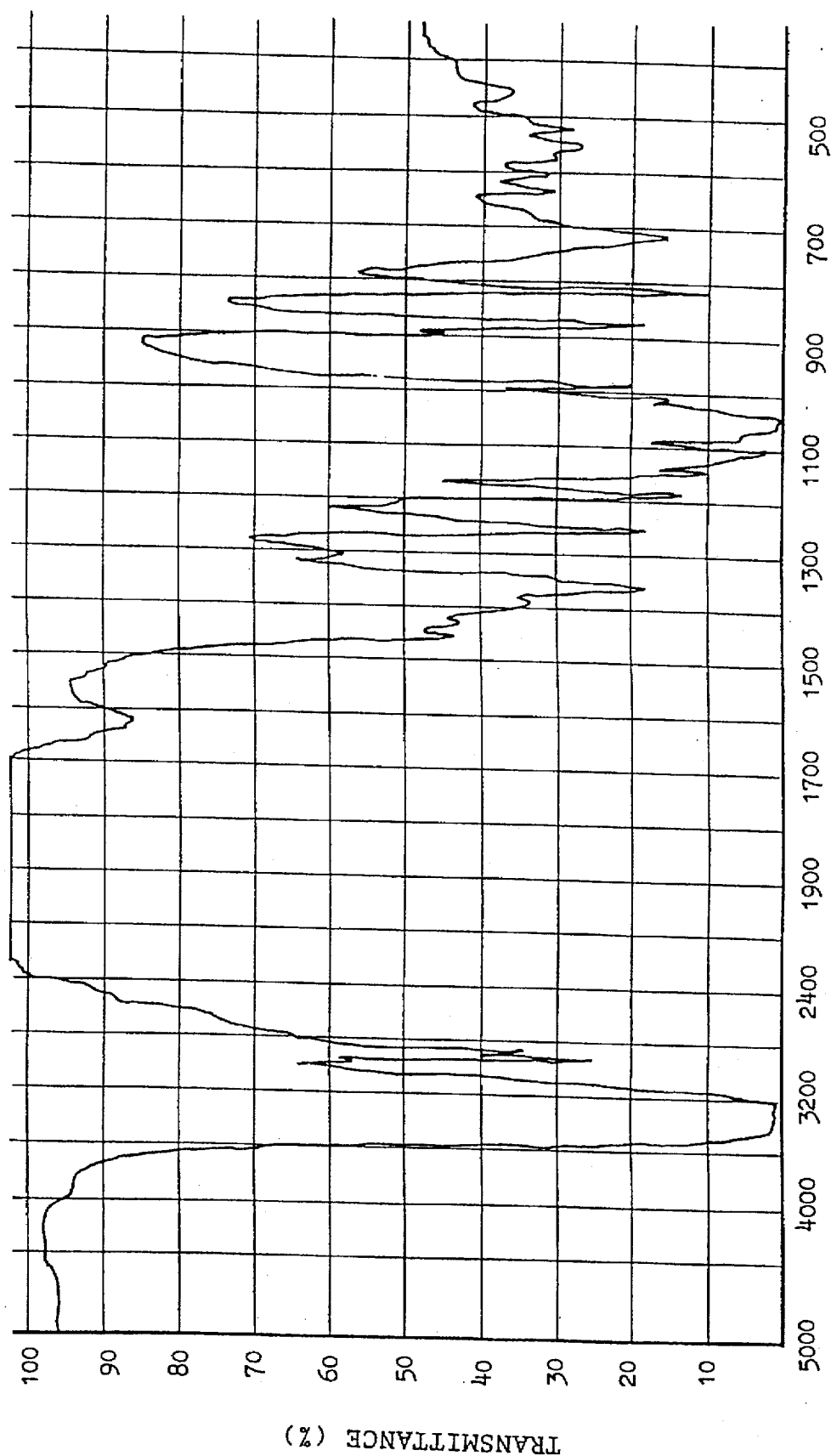
Figure 8:
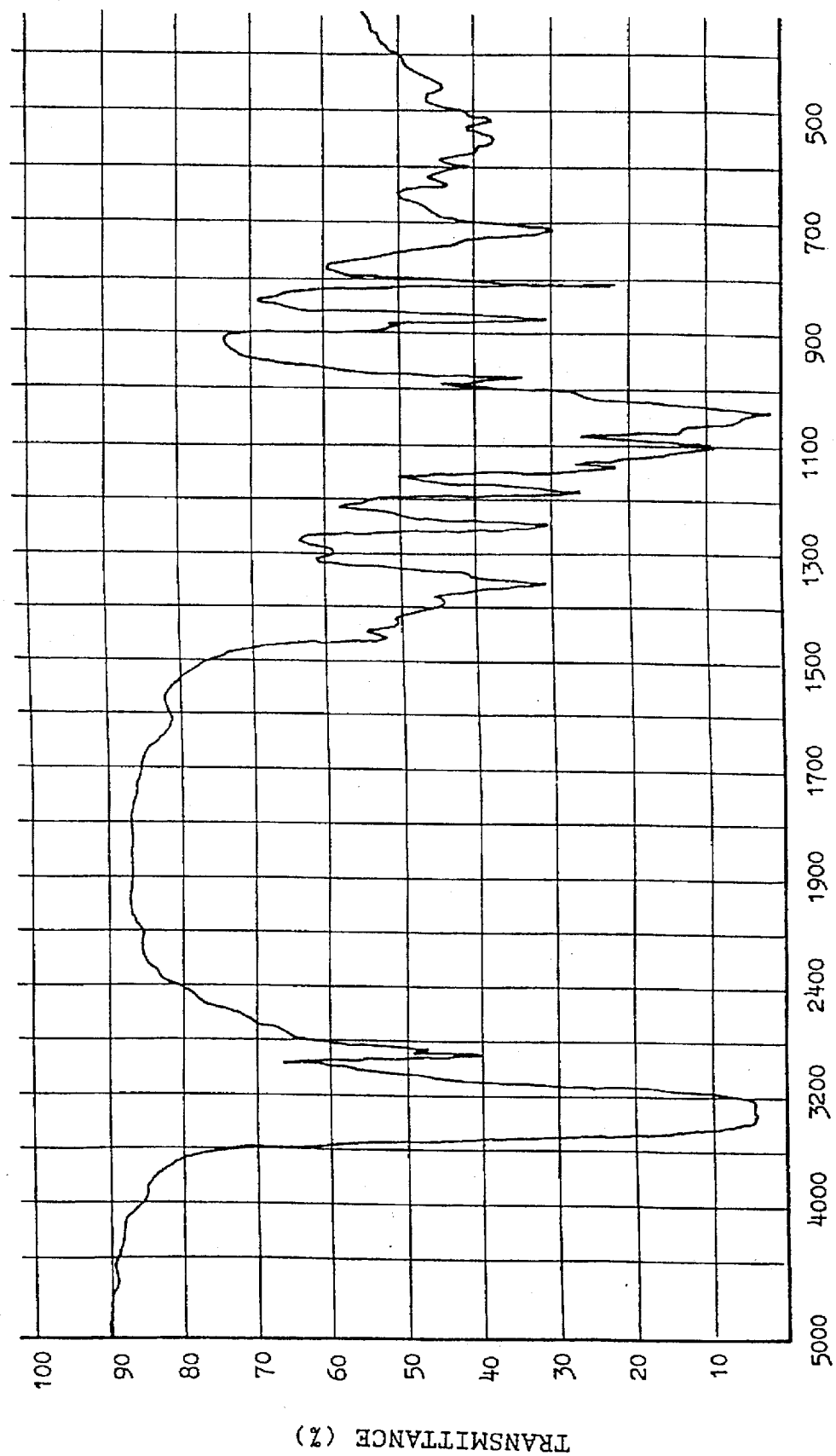

Five w/v % aqueous D-tagatose solution (pH 7.5) was added with 500 units/g D-tagatose of a partially purified enzyme solution which had been subjected to the purification steps up to the second fractionation using PEG in Example 1, and the mixture was enzymatically reacted at 40° C. for 30 hours. After completion of the reaction, the resultant reaction mixture was decolored with activated carbons in usual manner, demineralized with "Diaion SK1B (H-form)" and "Diaion WA30 (OH-form)", products of Mitsubishi Chemical Industries Ltd., Tokyo, Japan, and concentrated in vacuo to obtain about 60%, transparent syrup containing D-tagatose and D-sorbose. The syrup was separated and purified on a column chromatography using "Dowex 50W-X4", a strongly-acidic cation exchange of Dow Chemical Company, Midland, Mich., USA, concentrated, crystallized and separated to obtain a crystalline D-sorbose in the yield of about 55%. The physicochemical properties of the product were as follows: The melting point was 165° C. and the specific rotation was $[\alpha]^{20}_D=+44.0°$ (C=10%, $H_2O$). The infrared absorption spectrum (the datum of the product was shown in FIG. 7, and D-sorbose as a standard reagent was shown in FIG. 8.) had a good agreement with that of D-sorbose. Based on these results, the resultant saccharide converted from D-tagatose by the enzyme was D-sorbose. The product is favorably used as a sweetener, carbon source for fermentation, chemical regent, material and intermediate in chemicals and pharmaceuticals. The enzyme reaction is a reversible reaction, and because of this, D-tagatose is readily obtained when D-sorbose is used as a starting material.

EXAMPLE 3

Interconversion reaction of D-fructose and D-psicose

Ten w/v % aqueous D-fructose solution (pH 7.5) was added with 1,500 units/g D-fructose a partially purified enzyme solution which had been subjected to the purification steps up to the purification using DEAE-TOYOPEARL® in Example 1, and the mixture was enzymatically reacted at 45° C. for 30 hours. After completion of the reaction, the resultant reaction mixture was similarly as in Example 2, decolored, demineralized and concentrated in vacuo to obtain a transparent syrup containing D-psicose. The syrup was separated and purified on a column chromatography using a strongly-acidic cation exchange similarly as in Example 2 to obtain a syrupy D-psicose in the yield of about 25%, on a dry solid basis (d.s.b.). The physicochemical properties had a good agreement with those of the standard D-psicose. The product is favorably used as a sweetener, carbon source for fermentation, chemical regent, material and intermediate for chemicals and pharmaceuticals. The enzyme reaction is a reversible reaction, and because of this, D-fructose is readily obtained when D-psicose is used as a starting material.

EXAMPLE 4

Interconversion reaction of D-fructose and D-psicose

Ten w/v % aqueous D-fructose solution (pH 7.0) was added with 1,000 units/g D-fructose of a partially purified enzyme solution which had been subjected to the purification steps up to the second fractionation using PEG in Example 1, and the mixture was enzymatically reacted at 50° C. for 30 hours. After completion of the reaction, the resultant reaction mixture was similarly as in Example 2, decolored, demineralized and concentrated in vacuo to obtain a transparent syrup containing D-fructose and D-psicose in the yield of about 90%, d.s.b. The product is suitably used as a high-quality sweetener with a high sweetening-power, and advantageously used as a moisture-imparting agent, a crystallization-preventing agent and a gloss-imparting agent, as well as a sweetening agent for foods and beverages.

EXAMPLE 5

Interconversion reaction of D-xylulose and D-ribulose

One w/v % aqueous D-xylulose solution (pH 7.5) was added with 3,000 units/g D-xylulose of a partially purified enzyme solution which had been subjected to the purification steps up to the purification using DEAE-TOYOPEARL® in Example 1, and the mixture was enzymatically reacted at 35° C. for 50 hours. After completion of the reaction, the resultant reaction mixture was similarly as in Example 2, decolored, demineralized and concentrated in vacuo to obtain a transparent syrup containing D-ribulose. Similarly in Example 2, the syrup was separated and purified on a column chromatography using a strongly-acidic cation exchange to obtain a syrupy D-ribulose in the yield of about 20%, d.s.b. The physicochemical properties had a good agreement with those of the standard D-ribulose. The product is favorably used as a sweetener, carbon source for fermentation, regent, material and intermediate for chemicals and pharmaceuticals. The enzyme reaction is a reversible reaction, and because of this, D-xylulose is readily obtained when D-ribulose is used as a starting material.

EXAMPLE 6

Interconversion reaction of L-xylulose and L-ribulose

One w/v % aqueous L-xylulose solution (pH 7.5) was added with 3,000 units/g L-xylulose of a partially purified enzyme solution which had been subjected to the purification steps up to the purification using DEAE-TOYOPEARL® in Example 1, and the mixture was enzymatically reacted at 35° C. for 50 hours. After completion of the reaction, the resultant reaction mixture was similarly as in Example 2, decolored, demineralized and concentrated in vacuo to obtain a transparent syrup containing L-ribulose. Similarly as in Example 2, the syrup was separated and purified on a column chromatography using a strongly-acidic cation exchange to obtain a syrupy L-ribulose in the yield of about 20%, d.s.b. The physicochemical properties have a good agreement with those of the standard L-ribulose. The product is favorably used as a sweetener, carbon source for fermentation, chemical regent, material and intermediate for chemicals and pharmaceuticals. The enzyme reaction is a reversible reaction, and because of this, L-xylulose is readily obtained when L-ribulose is used as a starting material.

When the D-ketohexose 3-epimerase according to the present invention is allowed to act on free D-ketohexose, D-ketopentose and L-ketopentose, these ketoses are epimerized at their C-3 positions to readily form their corresponding epimeric D-ketohexose, D-ketopentose and L-ketopentose. The reaction system would open the way to an industrial-scale production of ketoses which has been deemed very difficult. Thus the finding of D-ketohexose 3-epimerase, and establishment of the preparation and uses have a great significance in the fields of saccharide-manufacturing industries, as well as food-, pharmaceutical- and cosmetic-industries.

While there has been described what is at present considered to be the preferred embodiments of the invention, it will be understood the various modifications may be made therein, and it is intended to cover in the appended claims all such modifications as fall within the true spirits and scope of the invention.

We claim:

1. A purified D-ketohexose 3-epimerase having the following physicochemical properties:

(a) Activity
   Epimerizing free D-=ketohexose at its C-3 position into its corresponding epimeric d-ketohexose; and epimerizing free D- and L- ketopentoses at their C-3 positions into their corresponding epimeric D- and L-ketopentoses;

(b) Optimum pH
   A pH of 7–10;

(c) pH stability
   Stable at a pH of 5–10;

(d) Optimum temperatures
   Around 60° C.;

(d) Thermal Stability
   Stable at a temperature of 50° C.;

(f) Ultraviolet absorption spectrum
   Exhibiting an absorption peak at a wavelength of 275–280 nm;

(g) Molecular weight
   41,000±3,000 daltons on gel filtration chromatography; and (h) Isoelectric point
   4.3±0.2; and (i) Specific Activity
   At least 359 units/mg protein.

2. A purified D-ketohexose 3-epimerase in accordance with claim 1 obtainable from *Pseudomonas cichorii* ST-24 (FERM BP-2736).

3. A process for preparing D-ketohexose 3-epimerase, which comprises:

(a) cultivating in a nutrient culture medium a bacterium, which is *Pseudomonas cichorii* ST-24 (FERM BP-2736), to produce D-ketohexose 3-epimerase; and (b) recovering the resultant D-ketohexose 3-epimerase of claim 1.

* * * * *